United States Patent [19]

Leiman et al.

[11] Patent Number: 4,762,125
[45] Date of Patent: Aug. 9, 1988

[54] BALLOON-TIPPED SUCTION CATHETER

[75] Inventors: Basil C. Leiman; Bruce D. Butler; Jeffrey Katz, all of Houston, Tex.

[73] Assignee: The University of Texas System, Houston, Tex.

[21] Appl. No.: 43,611

[22] Filed: Apr. 27, 1987

Related U.S. Application Data

[63] Continuation-in-part of Ser. No. 837,493, Mar. 7, 1986, abandoned.

[51] Int. Cl.⁴ ............................................. A61M 16/00
[52] U.S. Cl. ................................ 128/207.15; 604/96; 604/35
[58] Field of Search ................. 128/96, 101, 102, 167, 128/164, 256, 267, 35, 207.15

[56] References Cited

U.S. PATENT DOCUMENTS

| | | |
|---|---|---|
| 550,238 | 11/1895 | Allen . |
| 1,922,084 | 8/1933 | Gerow . |
| 2,642,874 | 6/1953 | Keeling . |
| 2,936,760 | 5/1960 | Gants . |
| 3,319,628 | 5/1967 | Halligan . |
| 3,799,173 | 3/1974 | Kamen . |
| 3,863,641 | 2/1975 | Popa ................................. 604/267 |
| 3,965,901 | 6/1976 | Penny et al. . |
| 3,977,408 | 8/1976 | MacKew . |
| 4,198,981 | 4/1980 | Sinnreich ......................... 604/101 X |
| 4,240,433 | 12/1980 | Bordow . |
| 4,416,273 | 11/1983 | Grimes . |
| 4,430,081 | 2/1984 | Timmermans .................... 604/167 X |
| 4,445,892 | 5/1984 | Hussein et al. ...................... 604/101 |
| 4,610,665 | 9/1986 | Matsumoto et al. ................ 604/256 |

OTHER PUBLICATIONS

Leiman, B. C., Hall, I. D. and Stanley, T. H., "Extirpation of Endotracheal Tube Secretions with a Fogarty Arterial Embolectomy Catheter", Anesthesiology 62, 847 (Jun. 1985).
Sontek Medical—Bodai Suction-Safe TM Swivel Y; Catalog No. SMI-1002 (Photographs Attached).
Leiman, B. C., Katz, J., Stanley, T. H., Luehr, S. and Butler, B. D., "Improved Secretion Removal with Less Blood Gas Alteration After Extirpation as Compared to Aspiration of Tracheobronchial Secretions", Anesthesiology 65, A159 (Sep. 1986).
Abstract of Presentation at the Annual Meeting of the Society of Anesthesiologists, made by Dr. Basil Leiman (Oct. 1986); Copies of Presentation Displays attached.
Leiman, B. C., Katz, J., Stanley, T. H., Luehr, S. and Butler, B. D., "Removal of Tracheal Secretions in Anesthetized Dogs: Balloon Catheters versus Suction", Anesthesia and Analgesia, 66:529–532 (Jun. 1987).

Primary Examiner—Stephen C. Pellegrino
Attorney, Agent, or Firm—Arnold, White & Durkee

[57] ABSTRACT

A balloon-tipped suction catheter, for extirpating and aspirating tracheobronchial secretions from the trachea, endotracheal tube or tracheostomy tube and a method for using such catheter. The catheter preferably embodies an elongated tube with a cannula extending along the elongated tube. The distal end of the cannula communicates with an expandable membrane or balloon which is attached either to the walls of the distal end of the elongated tube or directly to the distal end of the cannula. Proximal to the expandable membrane are apertures which provide fluid communication between the exterior and interior of the elongated tube. A control port is provided at the proximal end of the catheter to control the transmission of suction through the catheter.

In use, the catheter of this invention is inserted into an endotracheal tube, for example, to remove secretions. Positive end expiratory pressure ("PEEP") can be maintained by inserting the catheter through a "Y" connector assembly with a self-sealing diaphragm assembly. After the desired location is reached, the expandable membrane is inflated until it seals against the walls of the passageway. The control port is left uncovered until the membrane is inflated. The catheter is withdrawn and secretions are removed by the squeegee action of the balloon wall against the passageway wall and by aspiration.

5 Claims, 3 Drawing Sheets

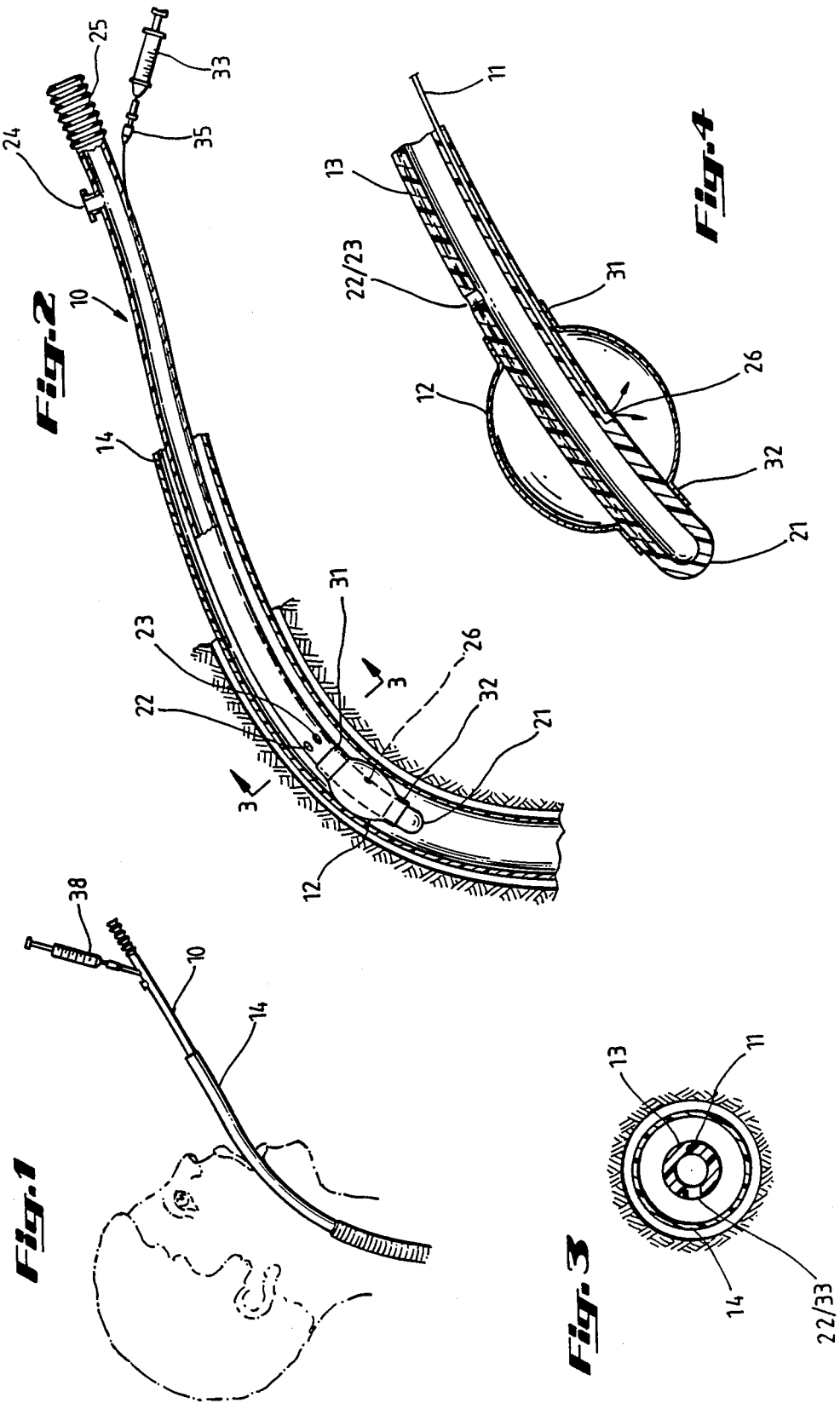

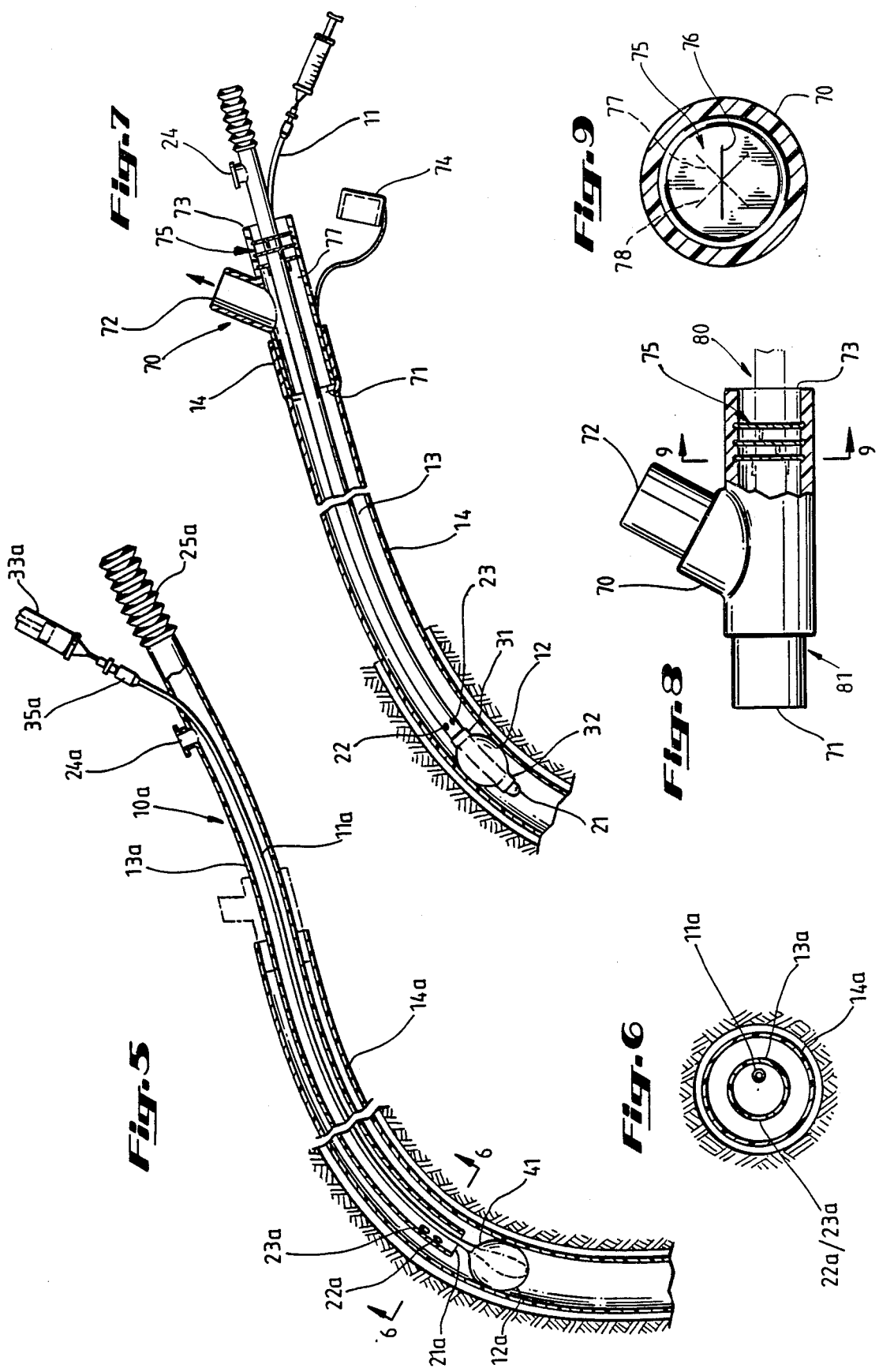

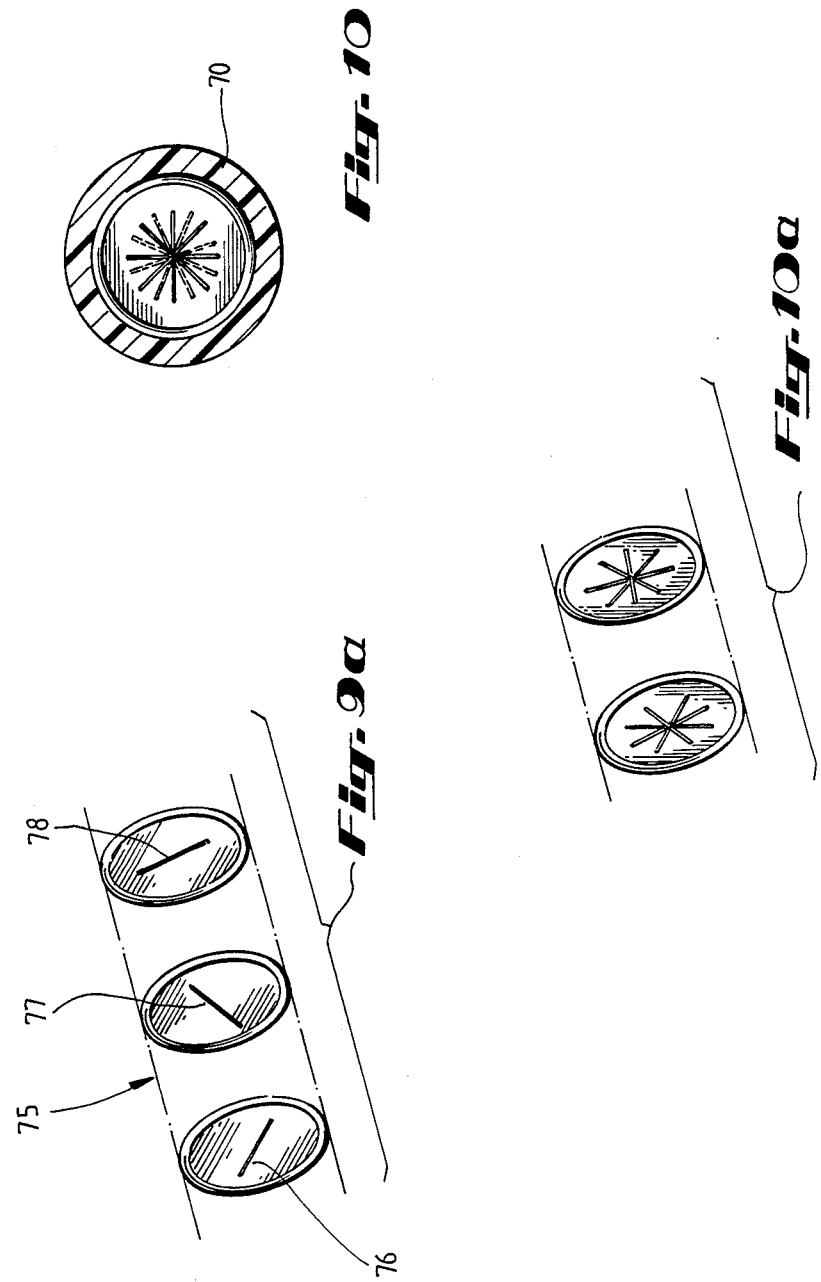

BALLOON-TIPPED SUCTION CATHETER

This application is a continuation-in-part of U.S. application Ser. No. 837,493, entitled Balloon-Tipped Suction Catheter, filed Mar. 7, 1986 now abandoned.

BACKGROUND OF THE INVENTION

This invention relates to catheters, and specifically ballon-tipped suction catheters, for aspiration and extirpation of mucus, secretions, and other deposits (hereinafter collectively referred to as "secretions") from the trachea, endotracheal tubes and tracheostomy tubes. In particular, the invention is directed to a catheter having an improved tip structure and an improved suction control structure which allow for the efficient removal of secretions, and which reduce the likelihood of trauma during the removal procedure. The invention also relates to a method for using such a catheter. The balloon-tipped suction catheter, when used in conjunction with a "Y" connector assembly containing a self-sealing diaphragm assembly is able to maintain positive end expiratory pressure ("PEEP") in the lungs.

Tracheobronchial secretions in endotracheal or tracheostomy tubes are usually removed by aspiration. This procedure, in which a suction catheter is passed down an endotracheal tube, may be ineffective, especially when secretions are viscid and adherent to the walls of the tube. Also, in spite of meticulous technique, this procedure is associated with complications. These complications include mucosal damage, hemorrhage and erosion of the tracheal mucosa. These disadvantages occur even in patients with diseases unrelated to pulmonary diseases.

U.S. Pat. No. 3,965,901, Penny et al., discloses a catheter containing side openings on its distal end. These openings are intended to improve the effectiveness of the catheter and reduce tissue damage. U.S. Pat. No. 4,240,433, Bordow, discloses a sharp tipped fluid aspiration needle with an inflatable balloon. The balloon can be inflated and positioned between the sharp tip of the needle and the internal organs during the aspiration procedure to minimize movement of the sharp needle and consequently reduce the risk of accidental puncture.

Another disadvantage of the above-described aspiration method is the inability to maintain PEEP in the lungs. During continuous mechanical ventilation of patients, a common clinical practice involves the use of PEEP wherein the ventilator provides a specific amount of pressure during the expiratory phase of ventilation. It is desirable not to lose the positive pressure established in the lungs during ventilation.

PEEP in the lungs can generally be lost during two steps of the aspiration method described above. First, PEEP may be lost during insertion of the catheter into the endotracheal tube. Exposure of the interior of the tube to atmospheric pressure causes the loss of the positive pressure. Various sealing means for maintaining pressure have been described. One means is a slidable balloon which surrounds the catheter. The catheter is positioned and the balloon is then slid against the opening to close the opening. A disadvantage of this sealing arrangement is that the user must manually move the slidable balloon to create the seal. Another sealing arrangement is described in U.S. Pat. No. 4,416,263, Grimes. Grimes discloses a connector valve assembly intended to maintain PEEP during the insertion and removal of a catheter. A check valve is used to prevent the loss of positive pressure.

Second, PEEP may be lost when suction is applied to the catheter to aspirate the body fluids. In an extreme situation, the conventional suction catheter can cause a lung to collapse due to the negative pressure created by the suction.

Balloon tipped catheters for treating the male urethra, including the prostate gland, have been disclosed. Generally, these catheters are described as being used for injecting or removing fluid from a specified area. One or two balloons are used to isolate the area to be treated. These catheters do not disclose any means for controlling the suction forces to insure that the area downstream of the treated area is not exposed to a vacuum. Control of these forces in the male urethra is not critical like it is in the endotracheal tube. It is important that the lungs are not collapsed by the suction forces applied through the catheter when inserted into the endotracheal tube.

Another problem that is not addressed by the catheters for treating the male urethra is removal of secretions that are strongly adherent to the walls of the passage or tube being cleaned. Secretions in the male urethra, such as pus, are not strongly adherent to the surface on which they lie. Therefore, the male urethra catheters generally describe aspiration as a suitable means for removal of the secretions. Secretions in the endotracheal tube are not easily removed by aspiration because they are strongly adherent to the walls of the endotracheal tube.

The disadvantages of aspiration can be avoided by removal of the secretions by extirpation. Extirpation may be accomplished by the use of a balloon-tipped catheter. The arterial embolectomy catheter sold under the trademark Fogarty TM may be used. The catheter is inserted into the endotracheal tube with the balloon deflated. When the desired position is reached, the ballon is inflated until it contacts the sides of the endotracheal tube. The catheter is pulled out of the endotracheal tube with the balloon inflated. As the catheter is withdrawn, the secretions along the walls of the endotracheal tube are displaced by the contact of the balloon against the tube walls. This is commonly referred to as a "squeegee" action. The squeegee action is especially helpful in removing secretions in the endotracheal tubes which are strongly adherent to the tube walls. As the balloon is withdrawn, the secretions accumulate on the proximal side of the balloon. The accumulated secretions are removed when the balloon exits from the endotracheal tube.

A disadvantage of extirpation is the efficiency of secretion removal. The secretions cannot be removed until the ballon has been completely withdrawn from the endotracheal tube. Consequently, the efficiency and ease of secretion removal decreases as the balloon is removed because of the increasing concentration of the secretions on the proximal side of the balloon.

The present invention addresses these disadvantages. This invention provides a balloon-tipped suction catheter and a method for using such a catheter that more efficiently and safely removes secretions from the trachea, endotracheal tubes and tracheostomy tubes. The catheter of the present invention is uniquely designed so that the advantages of both extirpation and aspiration can be utilized.

Another advantage of the present invention is that PEEP can be maintained in the lungs of the patient by using the balloon-tipped suction catheter in combination with a "Y" connector assembly having a self-sealing diaphragm assembly. The seal must be maintained at all times to maintain the pressure in the endotracheal tube. The self-sealing diaphragm assembly of the present invention retains its sealing ability throughout the insertion and removal of the catheter. The user does not have to contend with a sealing means which must be manipulated by the user to insure that the interior of the tube is not exposed to ambient pressure.

A third advantage of the present invention is that the operator can control the transmission of suction forces through the catheter. The operator can insure that suction is not applied at the distal end of the catheter until after the balloon is inflated sealing off the area downstream of the balloon.

SUMMARY OF THE INVENTION

This invention relates to a method and apparatus for the extirpation and aspiration of body secretions from the trachea, endotracheal tube and tracheostomy tube. The apparatus comprises a hollow elongated tube with distal and proximal ends. The distal end is inserted into the endotracheal tube which is to be cleaned. The tip of the distal end is rounded and soft to prevent tissue damage. The apparatus further comprises an expandable membrane, sometimes referred to as a balloon, located at the distal end thereof. The hollow elongated tube is typically constructed of any suitable material such as polyvinyl chloride. The expandable membrane is constructed of a flexible material, such as latex.

A cannula provides fluid communication at its distal end to the inside of the expandable membrane. The expandable membrane may be attached either directly to the outer walls of the distal end of the elongated tube or to the distal end of the cannula. Proximal to the expandable membrane are apertures in the walls of the elongated tube which provide for fluid communication between the exterior and interior of the tube. Mucus and other secretions may be aspirated through these apertures.

The proximal end of the elongated tube, the end that is not inserted into the body cavity, is connected to a negative pressure source. Negative pressure is provided in the ordinary manner known in the industry. A finger control port is provided at the proximal end of the elongated tube so that the operator can control the transmission of the suction forces to the distal end of the tube.

The proximal end of the cannula is connected to a positive pressure source that can provide sufficient pressure to inflate the expandable membrane. This positive pressure source is typically a syringe.

The catheter is inserted into an endotracheal tube while the expandable membrane is deflated. The finger control port is uncovered so that there is no suction being applied at the distal end of the catheter. After the desired position is reached, the expandable membrane is inflated until it contacts and seals against the walls of the endotracheal tube. Next, the catheter is withdrawn from the endotracheal tube causing secretions to be displaced from the walls of the tube by the squeegee action between the balloon and the tube walls. As the secretions accumulate on the proximal side of the expandable membrane, they are removed by aspiration through the apertures in the catheter walls. Aspiration is achieved by blocking off the finger control port by placing a finger over it.

In an alternate embodiment of this invention, the catheter is used in conjunction with a connector assembly, typically referred to as a "Y" connector, to maintain PEEP in the lungs during extirpation and aspiration with the balloon-tipped suction catheter. A first end of the connector assembly is connected snugly to an endotracheal tube or tracheostomy tube. A second end of the "Y" connector assembly, which is aligned with the first end, contains a self-sealing diaphragm assembly. The diaphragm assembly preferably contains three diaphragms in series. Each diaphragm contains a sliced opening. The sliced openings are arranged so that each slice is angularly displaced preferably about sixty degrees from the slices on the adjacent diaphragms. This offset of the sliced openings is critical for maintaining a pressure maintainable seal while inserting and removing the catheter. The diaphragms are typically constructed of latex. The third end of the connector assembly is connected to a conventional respiratory source which provides ventilation to the lungs.

In operation, the catheter is inserted through the self-sealing diaphragm assembly. The assembly seals against the catheter tube and guards against exposing the interior of the endotracheal tube to atmospheric pressure. Consequently, positive pressure is not lost inside the endotracheal tube. The respirator is not disconnected since the catheter is inserted through a separate port. The finger control part is open so that suction is not applied through the catheter. Suction is applied only after the expandable membrane has been inflated to seal against the walls of the endotracheal tube. Since the openings for aspiration are proximal to the expandable membrane, the positive pressure in the lungs is not dissipated by the suction forces.

Other advantages of this invention will be recognized from the description of the preferred embodiments which follow.

DESCRIPTION OF THE DRAWINGS

FIG. 1 is a side view of the catheter of the present invention being inserted into an endotracheal tube.

FIG. 2 is a sectional view showing the catheter of the present invention located in an endotracheal tube.

FIG. 3 is a detail sectional view taken along the line 3—3 in FIG. 2.

FIG. 4 is a detail sectional view of the expandable membrane of the preferred embodiment of the catheter.

FIG. 5 is a sectional view of an alternate embodiment of the present invention.

FIG. 6 is a detail sectional view taken along the line 6—6 of FIG. 5.

FIG. 7 is a sectional view showing the "Y" connector assembly in conjunction with the catheter of the present invention.

FIG. 8 is a sectional view of the "Y" connector assembly.

FIG. 9 is a detail sectional view taken along the line 9—9 of FIG. 8.

FIG. 9a is an exploded view of the diaphragm assembly.

FIG. 10 is a sectional view of an alternate embodiment of the diaphragm assembly.

FIG. 10a is an exploded view of the diaphragm assembly of FIG. 10.

DESCRIPTION OF THE PREFERRED EMBODIMENTS

A catheter 10, embodying the principles of the present invention, is shown in FIG. 2 to illustrate the presently preferred embodiment of the present invention. The catheter 10 embodies, in general, a cannula 11 having an expandable membrane 12 attached to the distal end thereof, with an elongated tube 13 surrounding the cannula 11. The elongated tube 13 may be of any suitable construction and is for the purpose of aspirating secretions in the trachea, endotracheal tube, or tracheostomy tube. It may be desirable to have the elongated tube 13 semirigid in construction.

The elongated tube 13, shown in FIG. 2, has a distal end 21 which is blocked and soft-tipped to prevent damage to body tissue. Proximal to the distal end 21 are apertures 22 and 23 in the wall of tube 13. The two apertures 22 and 23 are shown for purposes of illustration only. The number of apertures may be varied as needed. The proximal end 25 of the elongated tube 13 provides fluid communication with a conventional suction source. Transmission of suction forces to the apertures 22 and 23 is controlled, as discussed below, by operation of the control port 24. Preferably the elongated tube 13 is round in cross-sectional shape and of uniform cross-sectional area. For ease of insertion, the elongated tube 13 may be formed into a curve by any suitable method known in the industry.

The cannula 11 extends along the length of the elongated tube 13. The cannula 11 may be attached to the elongated tube 13 in various ways, some of which are discussed herein. One way is to anchor the cannula 11 to the elongated tube 13 at a proximal position and a distal position. A second way is to glue or fuse the cannula 11 to the elongated tube 13 by contentional means. A third way is to embed the cannula 11 in the wall of elongated tube 13 as shown in FIGS. 2 and 3. The cannula 11 is preferably uniform in cross-sectional area.

An expandable membrane or balloon 12 is attached to the walls of the elongated tube 13, as shown in FIG. 2. The expandable membrane 12 is attached to the elongated tube 13 on both the expandable membrane's proximal 31 and distal 32 sides. The expandable membrane 12 is preferably constructed of an expandable material such as latex. The expandable membrane remains deflated until a positive pressure is applied. The material of the expandable membrane 12 is flexible enough to expand to contact the walls of a body passage such as an endotracheal tube 14 within which the catheter is placed. The proximal end 35 of the cannula 11 is attached to a positive pressure source 33. Typically, this positive pressure source 33 is a syringe.

The distal end 26 of the cannula 11 comprises an opening that provides for fluid communication between the cannula 11 and the inside of the expandable membrane 12. As noted earlier, the distal end 21 of the elongated tube 13 is blocked and soft-tipped to prevent damage to body tissue. No fluid communication is possible through the distal end 21.

In an alternate embodiment of this invention, the expandable membrane 12a is anchored to the distal end of the cannula 11a at the juncture 41 as shown in FIG. 5. The juncture 41 may be formed by creating a seal between the expandable membrane 12a and the cannula 11a. The seal is conventional in the industry. Alternatively, the expandable membrane 12a and cannula 11a may be an integral structure that does not require a seal.

The distal end 21a comprises an opening which provides fluid communication between the exterior and interior of the elongated tube 13a. Secretions can be aspirated through the distal end 21a during the aspiration procedure discussed below.

The catheter 10, constructed in the aforementioned manner shown in FIG. 2, is inserted into an endotracheal tube 14, diagrammatically shown in FIG. 2, while the expandable membrane 12 is in the deflated position. The control port 24 is open so that suction is not transmitted to the distal end of the catheter 10. When the catheter 10 has reached the desired position in the endotracheal tube 14, positive pressure may be applied to the interior of the cannula 11 to cause the expandable membrane 12 to expand. The expandable membrane 12 is expanded until it is yieldingly held by the walls of the endotracheal tube 14.

Secretions on the walls of the endotracheal tube 14 are removed by pulling the catheter 10 out of the endotracheal tube 14 while the expandable membrane 12 is inflated. The squeegee action between the walls of the expandable membrane 12 and the endotracheal tube 14 causes the secretions which are strongly adherent to the walls to be displaced from the walls of the endotracheal tube 14.

The secretions that accumulate on the proximal side of the expandable membrane 12 as the membrane is withdrawn are removed by aspiration through the elongated tube 13. The suction source attached to the proximal end 25 of the elongated tube 13 is commonly known in the industry. Typically, suction is continuously provided to the proximal end 25. When suction is not desired at the apertures 22 and 23 of the elongated tube 13, the finger control port 24 is left uncovered. When suction is desired at the apertures 22 and 23, the port 25 can be blocked with the operator's finger. As secretions are displaced, they are drawn into the interior of the elongated tube 13 through the apertures 22 and 23.

The catheter 10 of this invention may be used in conjunction with a connector assembly, commonly referred to as a "Y" connector assembly 70, shown in FIG. 8, to maintain PEEP in the lungs of the patient. Distal end opening 71 is placed snugly inside an endotracheal tube 14 and provides communication with the interior of tube 14, as diagrammatically shown in FIG. 7. Side opening 72 provides for fluid communication with a respirator which provides oxygen to the patient. Proximal end opening 73 is the entrance through which the catheter 10 is inserted. The stopper 74 blocks the opening 73 when a catheter is not in use. The diaphragm assembly 75 is comprised of three flexible diaphragms. Each diaphragm contains a sliced opening. As shown in FIG. 9, the sliced openings 76–78 are preferably positioned so that they are angularly displaced about sixty degrees from the openings of the adjacent diaphragms. This offset positioning of the openings insures that the openings do not align and permit fluid communication through the assembly. The sliced openings of the diaphragm assembly permit the insertion of a catheter but do not permit fluid communication between the distal side 81 and proximal side 80 of the diaphragm assembly. FIG. 9a is an exploded view of the diaphragm assembly. The diaphragms are preferably mounted as close together as possible to insure a tight seal is maintained.

The single sliced openings 76–78 are shown in FIG. 9 for illustration only. Multiple slices on each diaphragm may also be provided as shown in FIG. 9. The diaphragms 76–78 are flexible and can be made of any suitable material, for example, latex.

In operation, the stopper 74 is removed from the opening 73 of the connector assembly 70. The catheter assembly 10 is inserted through the opening 73 and through the diaphragm assembly 75 as shown in FIG. 7. The expandable membrane 12 is deflated during insertion of the catheter 10. As the catheter assembly 10 is inserted, the diaphragm assembly 75 seals around the catheter 10 and guards against loss of positive pressure from the distal side 77 of the diaphragm assembly 75. After the catheter assembly 10 reaches the desired position, the expandable membrane 12 is inflated until it contacts the walls of the endotracheal tube 14. The expandable membrane 12 seals against the endotracheal tube 14 walls to inhibit fluid communication from the proximal side of the expandable membrane 12 to its distal side.

After the desired position is reached, extirpation and aspiration of the secretions is done in the manner described above. PEEP is maintained in the lungs of the patient because the expandable membrane 12 is yieldingly held by the walls of the endotracheal tube 14. The sealing contact between the expandable membrane 12 and the endotracheal tube 14 guards against the suction being applied to the lungs.

Suction may be controlled by a three-way valve rather than a finger control port as discussed above. The three-way valve guards against the suction forces being transmitted through the catheter 10 prior to inflation of the expandable membrane 12. Any suitable three-way valve available in the industry may be used. Operation of the three-way valve insures that PEEP is not lost due to aspiration during insertion of the catheter 10.

It may also be desirable to provide a safety mechanism to guard against the operator inadvertently applying suction to the catheter 10 prior to the complete inflation of the expandable membrane 12.

Although the preferred embodiments and method of use of this invention have been described hereinabove in some detail, it should be appreciated that these embodiments and methods of use are capable of variation and modification. The description of this invention is not intended to be limiting on this invention, but is merely illustrative of the preferred embodiments and methods of use of this invention. Other catheters and methods of use which incorporate modifications or changes to that which have been described herein and above are equally included within this application.

What is claimed is:

1. A catheter assembly for removing secretions from within an endotracheal or tracheostomy tube by extirpation or suction, comprising:
   (a) an endotracheal or tracheostomy tube with a distal end and a proximal end and sized to be inserted into a human, the distal end of said tube being configured to provide access to mucous in the throat or lungs and extending outside the mouth of the patient to said proximal end adapted to receive a catheter, the interior surface of said tube being adapted to slidably receive an elastomeric balloon;
   (b) a catheter adapted at its distal end to be inserted into the proximal end of said endotracheal or tracheostomy tube to a position within said tube, the proximal end of said catheter extending outside the proximal end of said tube;
   (c) an inflatable balloon mounted on and around the catheter at or near the catheter's distal end, said balloon capable of being inflated to the wall of the tube to form a slidable seal with the tube wall;
   (d) at least one aperture in the wall of the catheter proximate the proximal end of the balloon, capable of providing fluid communication between the interior of the catheter and the interior of said tube;
   (e) a cannula extending along the catheter connected at its distal end to the balloon and connectable at its proximal end to a pressure source suitable for inflating the balloon; and
   (f) a control port in the wall of the catheter near its proximal end for controlling transmission of suction forces to the distal end of said catheter.

2. The catheter assembly of claim 1 in which the inflatable balloon is mounted on and around the catheter.

3. The catheter assembly of claim 1 wherein the cannula is embedded in the wall of the catheter.

4. The catheter assembly of claim 1 further comprising a Y-connector assembly having a distal end opening aligned with a proximal end opening, a side opening and a diaphragm assembly, wherein said Y-connector is positioned around the catheter between said aperture and the control port such that the catheter extends through said Y-connector's two end openings, said distal end opening of said Y-connector adapted to be connected to the proximal end of the tube, said side opening of the Y-connector adapted to be connected to a respirator and said diaphragm assembly mounted within the Y-connector between the side opening and the proximal end opening of the Y-connector to seal the annulus between the catheter and the Y-connector.

5. The diaphragm assembly of claim 4 wherein said assembly comprises three diaphragms having sliced openings offset from each other.

* * * * *

UNITED STATES PATENT AND TRADEMARK OFFICE
CERTIFICATE OF CORRECTION

PATENT NO. : 4,762,125

DATED : Aug. 9, 1988

INVENTOR(S) : BASIL C. LEIMAN, BRUCE D. BUTLER and JEFFREY KATZ

It is certified that error appears in the above-identified patent and that said Letters Patent are hereby corrected as shown below:

On page 1, "Assignee: The University of Texas System, Houston, Tex." should read --Assignee: Board of Regents, The University of Texas System, Austin, Texas --.

In Column 1, line 66, "4,416,263" should read --4,416,273--.

In Column 6, line 68, "9" should read --10--.

Signed and Sealed this

Twenty-first Day of February, 1989

Attest:

DONALD J. QUIGG

*Attesting Officer*   *Commissioner of Patents and Trademarks*